United States Patent [19]

Sakamoto et al.

[11] Patent Number: 5,010,685
[45] Date of Patent: Apr. 30, 1991

[54] ARTIFICIAL SEED COMPRISING A SUSTAINED-RELEASE SUGAR GRANULE

[75] Inventors: Yuji Sakamoto, Tochigi; Seiichi Umeda; Hiroaki Ogishima, both of Saitama, all of Japan

[73] Assignee: Kirin Beer Kabushiki Kaisha, Tokyo, Japan

[21] Appl. No.: 345,897

[22] Filed: May 1, 1989

[30] Foreign Application Priority Data

May 2, 1988 [JP] Japan ................................. 63-109624

[51] Int. Cl.$^5$ .......................... A01C 1/06; A01C 21/00
[52] U.S. Cl. .......................................... 47/57.6; 47/58; 427/4; 127/29
[58] Field of Search ..................... 127/29, 30; 427/212, 427/4; 47/57.6, 58

[56] References Cited

U.S. PATENT DOCUMENTS

| | | | |
|---|---|---|---|
| 4,562,663 | 1/1986 | Redenbaugh | 47/58 |
| 4,583,320 | 4/1986 | Redenbaugh | 47/57.6 |
| 4,675,140 | 6/1987 | Sparks et al. | 424/492 X |
| 4,715,143 | 12/1987 | Redenbaugh et al. | 47/57.6 |
| 4,777,762 | 10/1988 | Redenbaugh et al. | 47/57.6 |
| 4,779,376 | 10/1988 | Redenbaugh | 47/57.6 |
| 4,780,987 | 11/1988 | Nelsen et al. | 47/57.6 |

Primary Examiner—Michael Lusignan
Attorney, Agent, or Firm—Limbach, Limbach & Sutton

[57] ABSTRACT

A sustained-release granule of sugar comprising a core comprising primarily one or more of a monosaccharide, a disaccharide and a trisaccharide and an outer film comprising 10-90% by weight of an ethylene-vinyl acetate copolymer and 90-10% by weight of a wax. This sustained-release granule of sugar may be prepared by coating a core comprising primarily one or more of a monosaccharide, a disaccharide and a trisaccharide with a coating material comprising 10-90% by weight of an ethylene-vinyl acetate copolymer and 90-10% by weight of a wax by spraying a solution of the coating material onto the core while tumbling or fluidizing the core. The sustained-release granule of sugar can be applied in an artificial seed comprising an active plant tissue and the sustained-release granule of sugar which are encapsulated in a gel matrix.

5 Claims, 4 Drawing Sheets

ARTIFICIAL SEED COMPRISING A SUSTAINED-RELEASE SUGAR GRANULE

BACKGROUND OF THE INVENTION

1. Field of the Art

This invention relates to a sustained-release granule which releases sugars of a low molecular weight depending on the temperature conditions of circumferential water, particularly the granule suitable for supplying nutrients to a plant meristematic tissue in an artificial seed.

2. Background Art

Recently, there have been successfully obtained plant bodies having a uniform and excellent character by the use of plant meristematic tissues such as a somatic embryo, an adventitious bud, a shoot primordium and a callus which are obtained by culturing a part of a tissue of a plant body. It is necessary to use such plant meristematic tissues in a seed analogue so that they will handle easily and can be stable physicochemically and biologically, and a sufficient supply of nutrients to them will be ensured until they grow by themselves by ingesting nutrients from their surrounding circumstances, in order to efficiently germinate, root and grow the plant meristematic tissues and to transport and plant in a green house or in a farm the plant meristematic tissues which have been cultured in a large scale in a factory. Such seed analogues containing the plant meristematic tissues are called artificial seeds, and some of them are specifically disclosed in, for example, Japanese Patent Laid-Open Publication Nos. 102308/84, 118103/85 and 2314811/85. The artificial seed is the product in which a plant meristematic tissue is encapsulated in a gel.

If a carbohydrate as an energy source is incorporated in a gel in the form of a high-molecular weight compound such as starch like the case of natural seeds in order to incorporate nutrients which correspond to endosperm into a gel, a plant meristematic tissue which lacks in an enzyme which decomposes such a high-molecular weight compound cannot grow by utilizing it. On the other hand, if a carbohydrate is incorporated in the gel in the form of a low-molecular weight compound such as sucrose or glucose for its easy and direct utilization and added in an amount sufficient to provide the whole nutrient needed for the growth of a plant meristematic tissue until it can ingest nutrients by itself from surrounding circumstances, the osmotic pressure becomes higher and water moves from the plant meristematic tissues into the gel so that the plant tissue will lower its growth and sometimes wither. For this reason, it is required to have a composition which will not release a nutrient of a low-molecular weight compound into the gel during storage but will gradually release the nutrient in 2 to 4 weeks after sowing, ideally a composition provided with a characteristic that the nutrient is supplied into the gel in such a manner that a suitable amount will be gradually supplied depending on the growth of a plant meristematic tissue. As to control of release of nutrients in an artificial seed, a method of using an adjuvant in the form of microcapsule is disclosed in Japanese Patent Laid-Open Publication No. 214811/85 which, however, only suggests a possibility and does not teach anything about the necessary properties or qualities regarding the microcapsule. Two examples of developments on microcapsules for an artificial seed are disclosed in "Hort. Science". 22, No. 5, 803-809 (1987), but a sustained-release of nutrients is not yet achieved in these examples.

On the other hand, the so-called "slow-acting fertilizer" which gradually releases fertilizer components from it scattered on a farm has been put to practical use, and it is described for example in Japanese Patent Publication No. 20371/69 that such a fertilizer is prepared by coating a mixture of an ethylene-vinyl acetate copolymer and a paraffin o fertilizer particles. However, the slow-acting fertilizers are designed to be stored in a dry state and gradually release fertilizer components after they are scattered and wetted. Thus, these fertilizers are not intended for their storage in a wet state and their release of fertilizer components which is controlled by temperature. Accordingly, these fertilizers do not give any suggestion as to whether it is possible to control release of contents by temperature.

SUMMARY OF THE INVENTION

The present invention provides a sustained-release granule of sugar comprising a core comprising primarily one or more of a monosaccharide, a disaccharide and a trisaccharide and an outer film comprising 10–90% by weight of an ethylene-vinyl acetate copolymer and 90–10% by weight of a wax.

The present invention also provides a process for producing such a sustained-release granule of sugar.

Thus, the process for producing a sustained-release granule of sugar according to the present invention comprises coating a core comprising primarily one or more of a monosaccharide, a disaccharide and a trisaccharide with a coating material comprising 10–90% by weight of an ehtylene-vinyl acetate copolymer and 90–10% by weight of a wax by spraying a solution of the coating material onto the core while tumbling or fluidizing the core.

According to the present invention, there is further provided an artificial seed comprising a plant meristematic tissue and the sustained-release granule of sugar which are encapsulated in a gel.

The present invention has been accomplished based on the finding that the above-mentioned coating material having the specific composition, in a state in contact with gel, exhibits a very temperature-dependent permeability to a low-molecular nutrient such as sucrose or glucose, and that a granule can be obtained which will not release the nutrient at a low temperature in a range of 0°–4° C. and gradually releases the nutrient at a temperature upon sowing of 20°–30° C. in a suitable amount according to the stage of growth of a plant meristematic tissue including germination and rooting by suitably adjusting the composition ratio and thickness of the coating material. Accordingly, if the sustained-release granule of sugar according to the present invention is incorporated in a gel of an artificial seed containing a plant meristematic tissue in the gel, the sugar will be released into the gel with the above-mentioned temperature dependence, meaning that such an artificial seed successfully overcomes the aforementioned drawbacks of the prior art.

BRIEF DESCRIPTION OF THE DRAWINGS

FIGS. 1 and 2 are the elution curves of sucrose at 4° C. and 25° C., respectively. FIG. 3 is the elution curve of sucrose when dipping the granule into water at 4° C. for 20 days and then raising the water temperature up to 25° C.

DETAILED DESCRIPTION OF THE INVENTION

Coating agent

Figure 1:
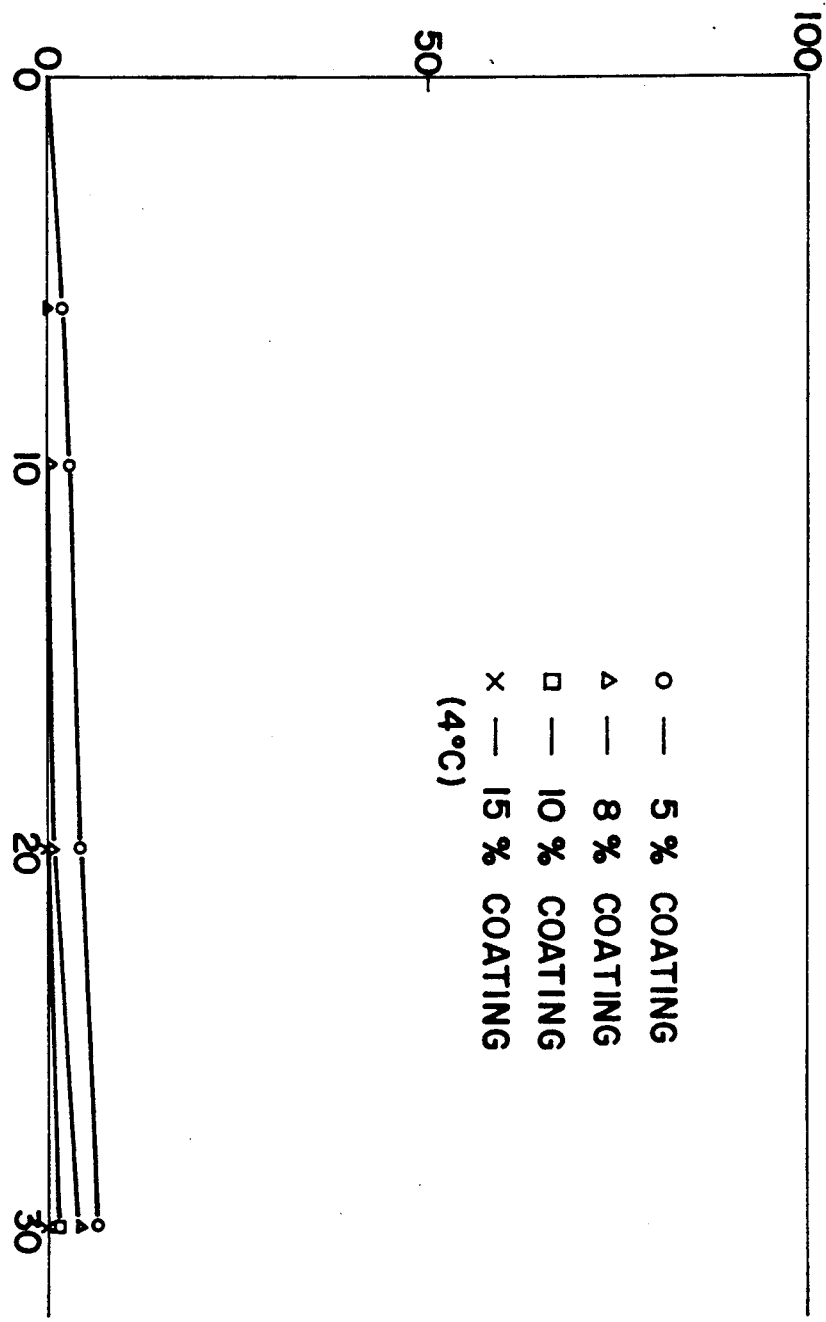
FIGS. 1–3 illustrate the amounts of sucrose eluted from sustained-release granules in water at predetermined temperatures.

The coating agent according to the present invention comprises primarily an ethylene-vinyl acetate copolymer and a wax.

The ethylene-vinyl acetate copolymer used in the present invention preferably contains 20-35% by weight, particularly 20-30% by weight of a vinyl acetate and has a number-average molecular weight preferably in the range of 20,000-40,000, particularly 25,000-35,000. The term "ethylene-vinyl acetate copolymer" herein includes a terpolymer which is prepared by copolymerizing a small amount of a third copolymerizable component in addition to the two essential components. An appropriate third monomer includes an acid, especially a carboxylic acid, and the terpolymer containing such an acidic monomer component is particularly preferred for the present invention. The copolymerization ratio of the acidic monomer may not be so high, and a ratio in the order of 1 mole % or less is usually sufficient. A ratio which will deviate the ethylene-vinyl acetate copolymer from its original properties is not preferred. The "acidic monomer" herein includes the same in its salt form deriving from the inherent nature of an acid.

The other essential component of the coating material according to the present invention is a wax. The term "wax" does not herein mean a wax as a strictly defined chemical terminology but refers substances that are called wax in a broad sense. Thus, the wax herein includes hydrophobic aliphatic compounds which are solid at an atmospheric temperature such as esters of a fatty acid with a higher mono- or di-hydric alcohol, fats, paraffins, higher alcohols, higher fatty acids. Preferably, the wax has a melting point in the range of 30°-70° C. Specific examples of the wax includes a commercially available paraffin having a melting point a specified above, cetyl alcohol, stearyl alcohol, lauric acid, Japan wax, beeswax and spermaceti.

The mixing ratio of the two components is preferably in the range of 10-90%, particularly 20-50% of the ethylene-vinyl acetate copolymer, with the balance of the wax. The use of the copolymer in an amount exceeding the above range, is not preferred since the sugar elutes too early and the coating material will be very sticky during preparation. On the other hand, if the amount of the copolymer is too low, the film formed by coating becomes brittle and may be damaged during its handling. In addition to the two main components, the coating material of the present invention may further comprises a small amount of other components, if desired. Such minor components are, for example, a plasticizer, a resin (particularly a water soluble one) or a filler.

Core

The core to be coated with the aforementioned coating material mainly comprises one or more of a monosaccharide, a disaccharide and a trisaccharide. Specific examples of the monosaccharide may include a hexose such as glucose, fructose, mannose or galactose, and a pentose such as arabinose, ribose and xylose; and specific examples of the disaccharide may include sucrose, maltose and lactose; and specific examples of the trisaccharide may include raffinose, maltotriose and melezitose. These sugars may be used singly or as a mixture thereof. The sugar may be coated as it is in its crystal form with the aforementioned coating material, or in the form of its powder or granules formed from the powder and additional components, or in the form of particles formed of a solution or gel containing the sugars. Usually, coating is preferably carried out on the crystals or the nearly spherical granules of sugar.

In addition to the above mentioned sugars, the core of the present invention may further comprises other components, according to necessity or application. When the sustained-release granule according to the present invention is used in an artificial seed, it is desirable to add as the core components inorganic salts and urea which will provide nutrients other than sugar such as nitrogen, phosphoric acid and potassium, or plant hormones.

The size of the sustained-release granule according to the present invention is not particularly limited. However, when used in an artificial seed, the granule size is preferably in the range of 0.1 mm-2 mm in diameter for incorporation of the granule into the gel. In this case, it is preferred that one granule having a diameter of ca. 1 mm-2 mm is incorporated into every artificial seed, or 20-500 granules having a diameter of ca. 0.2 mm-0.7 mm are incorporated in the capsule in such a manner that they are dispersed in a solution that forms gel or they are located in the neighborhood of an encapsulated plant meristematic tissue.

Production of the sustained-release qranule

The sustained-release granule according to the present invention can be produced by any appropriate method.

It is desirable for the production of the sustained-release granule to form a film as uniform as possible on the surface of the core (which, as apparent from the above description, is not always limited to a solid particle). For this purpose, the film is preferably formed by placing the core in a tumbling granulating and coating apparatus equipped with a rotating plate, and spraying a solution of the coating material onto the core while tumbling the core, or by charging the core in a fluidized bed and spraying a solution of the coating material onto the core while fluidizing the core by blowing air, etc., into the fluidized bed.

Application of the sustained-release granule

The sustained-release granule according to the present invention can be incorporated into the gel in an artificial seed to play a role as the endosperm of the artificial seed or can be incorporated into an agar culture medium or a liquid culture medium, where the sustained-release granule performs the temperature-dependent release of sugars.

An example of such applications is an artificial seed. The artificial seed is well-known and generally comprises a plant meristematic tissue which is encapsulated in a gel. The gel in this case is, for example, an alginic acid salt, agar or the like, and preferably contains nutrients or plant hormones necessary for the germination, rooting or growth of the plant meristematic tissue.

Figure 2:
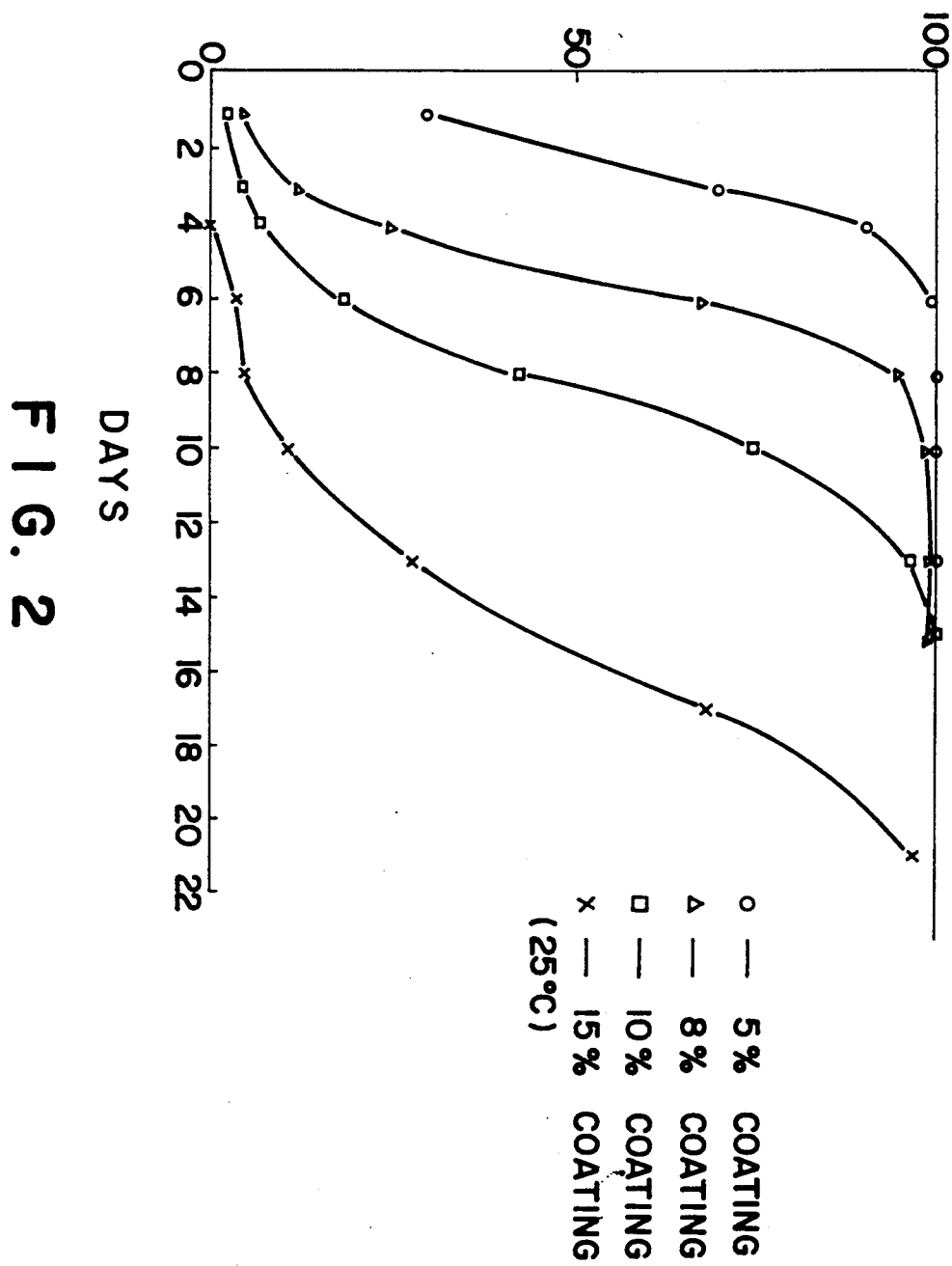
Figure 3:
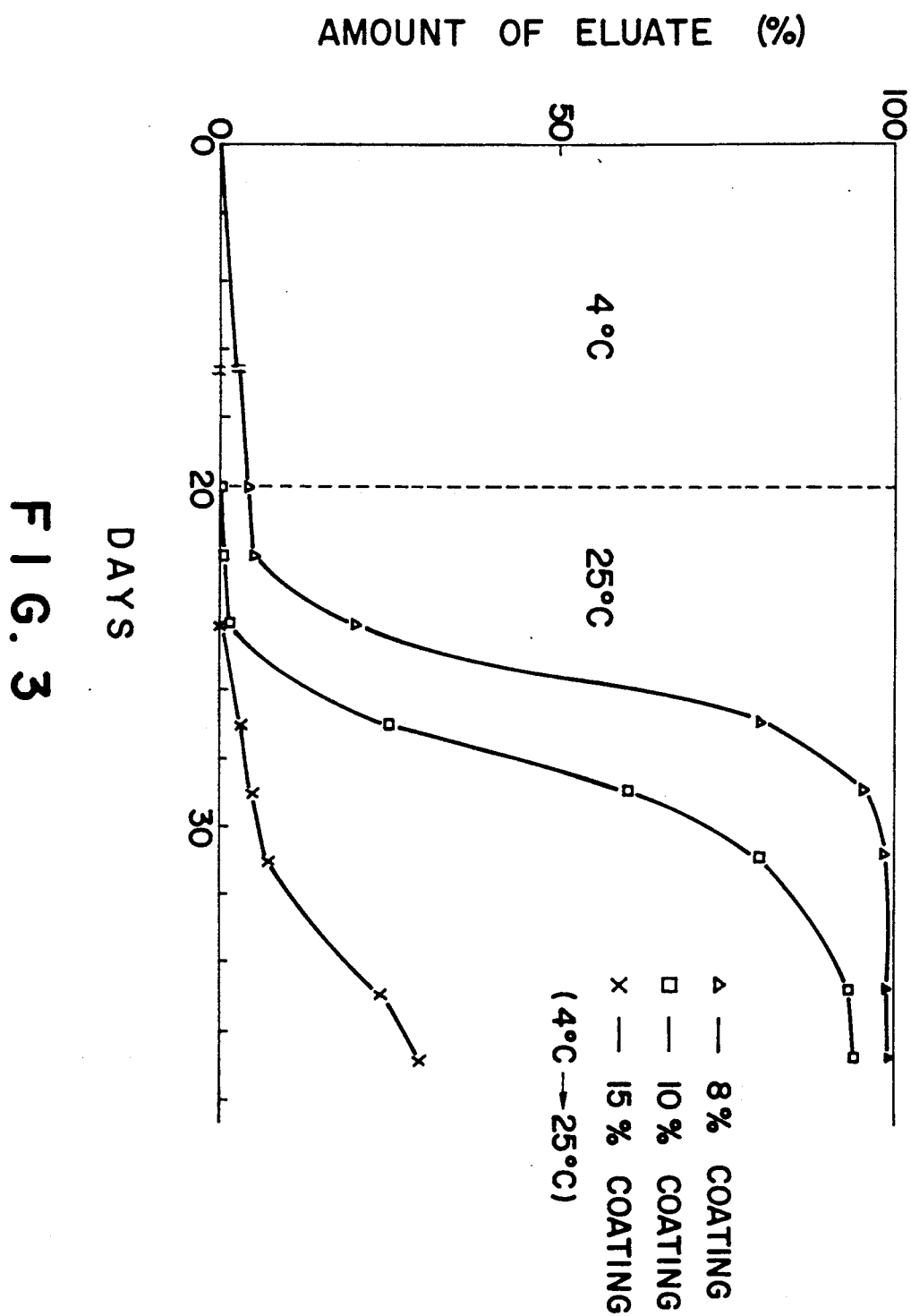

The artificial seed as one of applications of the sustained-release granule of sugar according to the present invention contains at least one piece of the sustained-release granule in the gel of the above mentioned well-known artificial seed. The artificial seed according to the present invention contains a component, which should not exist in the gel from the first or in a high concentration, in the sustained-release granule, i.e. separately from the plant meristematic tissue, and the component can be released gradually depending upon temperature.

using a refractometer. The results are shown in FIGS. 1 and 2. FIG. 3 shows the amount of sucrose eluted after dipping the granules in water at 4° C. for 20 days and then raising the temperature of water up to 25° C.

EXAMPLES 2-8 AND COMPARATIVE EXAMPLES 1-6

Onto the same sucrose granules as in Example 1, coating was carried out with various coating materials. The coated granules were dipped in water at 4° C. and 25° C., and the amount of sucrose eluted were determined. The results are shown in Table 1.

TABLE 1

| | High-molecular weight substance | | Wax | | Coating amount (% based on sucrose) | Elution rate of sucrose | | Remarks |
|---|---|---|---|---|---|---|---|---|
| | Name | Formulating ratio*1 | Name | Formulating ratio*1 | | 4° C., 20 days | 25° C., 10 days | |
| Example | | | | | | | | |
| 2 | Elvax 4260 | 60 | Beeswax | 40 | 8 | 10.0 | 83 | |
| 3 | Elvax 360 | 40 | Beeswax | 60 | 10 | 5.2 | 81 | |
| 4 | Elvax 360 | 30 | Paraffin (mp 57° C.) | 70 | 10 | 3.5 | 85 | |
| 5 | Elvax 250 | 30 | Paraffin (mp 57° C.) | 70 | 12 | 3.0 | 72 | |
| 6 | Elvax 4355 | 60 | Spermaceti | 40 | 8 | 8.7 | 94 | |
| 7 | Elvax 4355 | 35 | Cetyl alcohol | 65 | 10 | 6.6 | 78 | |
| 8 | Elvax 4260 | 30 | Lauric acid | 70 | 10 | 4.7 | 80 | |
| Comparative Example | | | | | | | | |
| 1 | Elvax 4260 | 100 | — | — | 10 | 85 | Not tested | Slightly sticky |
| 2 | — | — | Beeswax | 100 | 10 | 100 | Not tested | Brittle |
| 3 | Ethyl cellulose | 45 | Shellac MYVACET*3 | 45 10 | 20 | 92 | Not tested | |
| 4 | Acrylate resin*2 | 100 | — | — | 15 | 98 | Not tested | Slightly sticky |
| 5 | Polyvinyl acetate | 100 | — | — | 15 | 96 | Not tested | Slightly sticky |
| 6 | Polyvinyl acetate | 30 | Beeswax | 70 | 15 | 100 | Not tested | |

*1Ratio in solid contents.
*2Copolymer mainly comprising poly(methyl acrylate).
*3Trade name.

EXAMPLE 1

500 grams of spherical granules of sucrose having a size of 42-60 mesh were charged into a centrifugal tumbling granulating and coating apparatus (CF-360, manufactured by Freund Industrial Co., Ltd.), and coating was carried out by spraying at a rate of 10 ml/min a solution of a coating material comprising 1 part by weight of an ethylene-vinyl acetate-carboxylic acid copolymer ("Elvax 4260", manufactured by du Pont, vinyl acetate content: 28% by weight, acid value: 6, melt index: 6 g/10 min) and 3 parts by weight of beeswax ("BWS-30", manufactured by NODA WAX K.K.) in 96 parts by weight of trichloroethylene. During the coating, the rotation plate of the apparatus was rotated at a rate of 160 rpm, air was blown at a rate of 350 liter/min, and the temperature of the air was set at 50° C. After spraying a predetermined amount of the coating material, the coated granule was taken out and dried overnight.

Thus, granules having the coating material in an amount of 5%, 8%, 10% and 15% based on the amount sucrose were prepared. A given amount of the granules were dipped into a given amount of water at 25° C. and 4° C., in such a manner that the water will form a solution having a sucrose concentration of 5% when the whole amount of sucrose in the granules is eluted. Thereafter, the amount of sucrose eluted was determined. The concentration of sucrose was measured

EXAMPLE 9

Coated granules having a coating in an amount of 12% were obtained in the same manner as in Example 1 except that granulated sugar of a size of 48-70 mesh which had been passed through a screen was used. The proportion of sucrose eluted after dipping the granule in water at 4° C. for 20 days was 2.1%, and 78% at 25° C. for 10 days.

EXAMPLE 10

Coated granules having a coating in an amount of 6% was obtained in the same manner as in Example 1 except that spherical granules of glucose of a size of 32–48 mesh which had been passed through a screen were used. The proportion of glucose eluted after dipping the granule in water at 4° C. for 20 days was 1.6%, and 59% at 25° C. for 10 days.

EXAMPLE 11

In a fluidized bed granulating and coating apparatus (FL-5, manufactured by Freund Industrial Co., Ltd.) was charged 4 kg of the spherical sucrose granules used in Example 1, and coating was carried out by spraying at a rate of 110 ml/min the same solution as in Example 1 while fluidizing the granules by blowing air at a rate of 3 m³/min at 60° C. to obtain coated granules having a coating in an amount of 10% (per sucrose granule). The proportion of sucrose eluted after dipping the granule in water at 4° C. for 20 days was 2.5%, and 87.7% at 25° C. for 10 days.

EXAMPLE 12

A leaf section of celery (*Apium graveoleus* L.) was sterilized with 70% ethanol and 0.5% aqueous solution of sodium hypochlorite and placed on a Schenk and Hildebrandt (SH) agar medium containing 2.0 ppm of 2,4-dichlorophenoxyacetic acid (2,4-D) and 0.5 ppm of kinetin and cultured at 25° C. for 30 days to obtain a callus. The callus was transferred on a hormone-free SH agar medium to obtain a somatic embryo. The sustained-release granules of sucrose obtained in Example 1 (having a coating amount of 8% relative to sucrose) was sterilized with chlorine gas. The sustained-release granules thus sterilized in amounts of 1 g, 3 g, 6 g and 12 g, respectively, were uniformly dispersed in 100 ml of 2% (w/v) aqueous solution of sodium alginate ("Protanal LF-60", manufactured by Protan) which had been sterilized in an autoclave [the weight represented by gram of the sustained-release granules added to 100 ml of the aqueous sodium alginate solution is indicated hereinafter as the sustained-release granule content (%)]. In this solution was further dispersed the aforementioned somatic embryos, and the dispersion thus formed was dropped into a 100 mM calcium chloride solution to obtain spherical beads. The beads thus produced were left standing in the same solution for 20 minutes to be hardened. Next, the beads each containing one somatic embryo were taken out and placed in a sterilized water for 10 minutes to prepare an artificial seed which contained the sustained-release granule as well as the celery adventitious embryo. The artificial seed was placed on a polyester fiber cube for hydroponic culture (50×50×20 mm, manufactured by Toyobo) in a culturing container "PLANT BOX" (manufactured by Verde Co., Ltd.), and cultured in a growth chamber which was set up at 20° C. and 13,000 lux/12 hours of photoperiod. On the culturing, a sucrose-free SH liquid culture medium was used as the culturing medium in an amount of 50 ml per "PLANT BOX". The results after 3 weeks are listed on Test Nos. 1-4 in Table 2. The sustained-release granule of sucrose was effective for the germination and growth of celery, and it was germinated at high rate of 90% and 85% for the sustained-release granule contents of 6% and 12%, respectively.

COMPARATIVE EXAMPLE 7

An artificial seed of a celery somatic embryo was prepared using an aqueous solution of sodium alginate containing no sustained-release granule of sucrose in the same way as in Example 12. The artificial seed was cultured in a sucrose-free SH liquid culture medium in the same manner as in Example 12. As a result thereof, the germination rate was 30% and its growth was also bad (Test No. 5 in Table 2).

COMPARATIVE EXAMPLE 8

In Comparative Example 7, the artificial seed was dipped into a SH liquid culture medium containing 3% of sucrose and then cultured in a sucrose-free SH liquid culture medium. As a result thereof, the germination rate was 20% (Test No. 6 in Table 2).

COMPARATIVE EXAMPLE 9

In Comparative Example 7, when culturing was conducted with SH liquid culture medium containing sucrose in an amount of 3%, 6% and 12%, the germination rates were 70%, 50% and 20%, respectively. Unlike the case of Example 12, a remarkable inhibition of growth was observed at the high concentrations of sucrose (6% and 12%) (Test Nos. 7-9 in Table 2).

EXAMPLE 13

Figure 4:
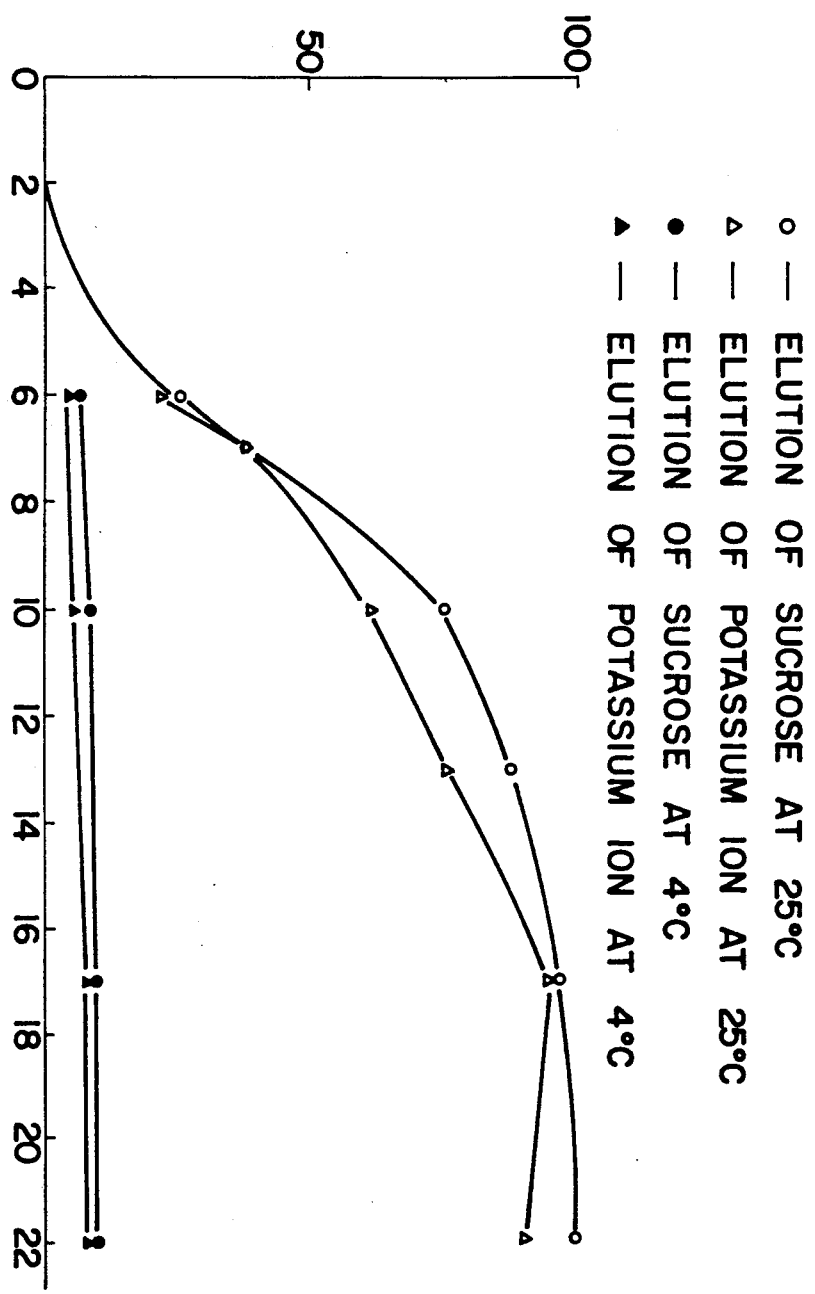
FIG. 4 illustrates the amounts of sucrose and a potassium ion eluted from the sustained-release granule prepared in Example 13 at 4° C. and 25° C.

In Example 1, 500 g of spherical granules of sucrose were charged into a centrifugal tumbling granulating and coating apparatus (CF-360), and granulation was conducted while spraying 250 g of powderous sugar ("ANTILOCK", manufactured by Freund Industrial Co., Ltd.) and 25 g of "HYPONEX FINE POWDER" [manufactured by HYPONEX, USA; a product by further milling with a "JET-MILL TJ-60" (manufactured by Freund Industrial Co., Ltd.)] together with a 60% syrup as a binder onto the granules. The product thus formed was dried using a fluidized bed granulating and coating apparatus "FL-MINI" (manufactured by Freund Industrial Co., Ltd.; at a blowing air temperature of 90° C./10 minutes) and then passed through a screen (32 mesh) to obtain a core. Coating was carried out on the core in the same manner as in Example 1. The amount of sucrose eluted from the coated granule having a coating amount of 10% was determined at 4° C. and 25° C. Also, the amount of potassium ion eluted from the coated granule was determined as a typical index for observing the elution of "HYPONEX". Determination was conducted with a refractometer for the sucrose concentration and with an atomic-absorption spectrophotometer for the potassium ion concentration, respectively. The results are shown in FIG. 4.

EXAMPLE 14

An artificial seed was prepared in the same manner as in Example 12, except that the sustained-release granule obtained in Example 13 was used in place of the sustained-release granule of sucrose. When the artificial seed was cultured in distilled water as a culturing medium instead of the sucrose-free SH liquid culture medium, germination rates were 45%, 85%, 90% and 80% with the presence of the sustained-release granules in the amounts of 1%, 3%, 6% and 12%, respectively (Test Nos. 10, 11, 12 and 13 in Table 2).

COMPARATIVE EXAMPLE 10

In Example 14, an artificial seed containing no sustained-release granule was prepared. When this artificial seed was cultured in distilled water as a culture solution, the celery withered without germination (Test No. 14 in Table 2).

EXAMPLE 15

In Example 12, an artificial seed containing a lettuce adventitious bud in place of the celery somatic embryo was prepared. Thus, a leaf section of lettuce (*Lactuca sativa* L.) was sterilized with 70% ethanol and 0.5% aqueous solution of sodium hypochlorite and placed on a Murashig and Skoog (MS) agar medium containing 1.0 ppm of parachlorophenoxyacetic acid (PCPA) and 0.5 ppm of benzyladenine (BA) and cultured at 25° C. for 30 days to obtain a callus. The callus was transferred on an MS agar culture containing 0.1 ppm of PCPA and 0.2 ppm of BA to induce adventitious buds. Each adventitious bud was taken out and cultured on a hormone-free MS agar medium to a height of 3-4 mm. The bud thus cultured was used as a content of an artificial seed. In the same manner as in Example 12, artificial seeds were prepared with aqueous sodium alginate solutions containing the sustained-release granules in the amounts of 1%, 3%, 6% and 12%, respectively. These artificial seeds were cultured in the same manner as in Example 12 except that a 1/1000 dilution of "HYPONEX FINE POWDER" was used as a culture solution in place of the sucrose-free SH liquid culture medium. Lettuces were all germinated, and their leaves were dark green (Test Nos. 1-4 in Table 3).

COMPARATIVE EXAMPLE 11

In Example 15, an artificial seed of a lettuce adventitious bud was prepared using an aqueous sodium alginate solution containing no sustained-release granule of sucrose. When this artificial seed was cultured in the same manner as in Example 15, the germination rate was equal to that in Example 15, but the growth was relatively poor (Test No. 5 in Table 3).

EXAMPLE 16

When cultivation was conducted with decreasing the luminous intensity from 13,000 lux to 2,000 lux in Example 15, germination was as good as in Example 15 (Test Nos. 6-9 in Table 3).

COMPARATIVE EXAMPLE 12

When the luminous intensity was decreased from 13,000 lux to 2,000 lux in Comparative Example 11, the growth of the plant was extensively delayed (Test No. 10 in Table 3).

EXAMPLE 17

The artificial seeds of the lettuce adventitious bud obtained in Example 15 were stored at 4° C. for 30 days and then cultured in the same manner as in Example 15. As a result, the germination rate was 100%, but the growing rate was slightly slower as compared with the case where no storage of the adventitious bud was conducted (Test Nos. 11-14 in Table 3).

COMPARATIVE EXAMPLE 13

The artificial seeds of the lettuce adventitious bud obtained in Comparative Example 11 were stored at 4° C. for 30 days and then cultured in the same manner as in Comparative Example 11. As a result, the germination rate was as low as 20%, and the growth was also inhibited (Test No. 15 in Table 3).

EXAMPLE 18

In Example 15, artificial seeds were prepared using the sustained-release granule prepared in Example 13 instead of the sustained-release granule of sucrose. When the artificial seeds were cultivated in distilled water instead of a 1/1000 dilution of the "HYPONEX", all of the seeds were germinated although the growth was somewhat bad (Test Nos. 16-19 in Table 3).

COMPARATIVE EXAMPLE 14

When the artificial seeds obtained in Comparative Example 14 were cultivated in the same manner as in Example 18, lettuces were all withered without germination (Test No. 20 in Table 3).

EXAMPLE 19

In Example 12, an artificial seed containing therein a carrot somatic embryo instead of the celery somatic embryo was prepared. Thus, a hypocotyl section of a seedling of a carrot (*Daucus carota* L.) is placed on an MS agar medium containing 1 ppm of 2,4-D and cultured at 25° C. for 3 weeks to obtain a callus. The callus was transferred and cultured in a hormone-free MS liquid culture medium to obtain a carrot somatic embryo. An artificial seed containing this somatic embryo was prepared in the same manner as in Example 12. Cultivation test wa conducted in the same manner as in Example 12 except that an MS liquid culture medium was used as a culture solution instead of the SH liquid culture medium. As the result, germination rate was 100%, 90% and 80% for the sustained-release granule in the amounts of 3%, 6% and 12%, respectively (Test Nos. 1-4 in Table 4).

COMPARATIVE EXAMPLE 15

In Example 19, an artificial seed of a carrot somatic embryo containing no sustained-release granule of sucrose was prepared. When the artificial seeds were grown in the same manner as in Example 19, germination rate was 10% (Test No. 5 in Table 4).

TABLE 2

Germination state of the artificial seed containing a celery somatic embryo

| Test No. | Content of sustained-release granule | Culture medium | State of growth after 3 weeks | | Evaluation of growth* |
|---|---|---|---|---|---|
| | | | Colored green | Germinated | |
| 1 | Sustained-release granule of sucrose with 8% coating, 1% | Sucrose-free SH liquid culture medium | 10/20 | 7/20 | 2 |
| 2 | Sustained-release granule of sucrose with 8% coating, 3% | Sucrose-free SH liquid culture medium | 9/20 | 9/20 | 3 |
| 3 | Sustained-release granule of sucrose with 8% coating, 6% | Sucrose-free SH liquid culture medium | 19/20 | 18/20 | 4 |
| 4 | Sustained-release granule of sucrose with 8% coating, 12% | Sucrose-free SH liquid culture medium | 17/20 | 17/20 | 4 |
| 5 | Not contained | Sucrose-free SH liquid culture medium | 10/20 | 6/20 | 2 |
| 6 | Not contained (3% sucrose solution) | Sucrose-free liquid culture medium | 4/20 | 4/20 | 1 |
| 7 | Not contained | SH liquid culture containing 3% sucrose | 8/20 | 14/20 | 3 |
| 8 | Not contained | SH liquid culture containing 6% sucrose | 6/20 | 10/20 | 2 |
| 9 | Not contained | SH liquid culture containing 12% sucrose | 0/20 | 4/20 | 1 |
| 10 | Sustained-release granule of | Distilled water | 9/20 | 9/20 | 3 |

TABLE 2-continued

Germination state of the artificial seed containing a celery somatic embryo

| Test No. | Content of sustained-release granule | Culture medium | State of growth after 3 weeks | | Evaluation of growth* |
|---|---|---|---|---|---|
| | | | Colored green | Germinated | |
| 11 | sucrose with 8% coating and Hyponex, 1% Sustained-release granule of sucrose with 8% coating and Hyponex, 3% | Distilled water | 16/20 | 17/20 | 4 |
| 12 | Sustained-release granule of sucrose with 8% coating and Hyponex, 6% | Distilled water | 17/20 | 18/20 | 4 |
| 13 | Sustained-release granule of sucrose with 8% coating and Hyponex, 12% | Distilled water | 16/20 | 16/20 | 3 |
| 14 | Not contained | Distilled water | 0/20 | 0/20 | 1 |

*1, Withered; 2, Inhibition of growth; 3, poor growth; 4, Slightly poor growth; 5, Normal.

TABLE 3

Germination state of the artificial seed containing a lettuce adventitious bud

| Test No. | Content of sustained-release granule | Culture medium | Light condition during growth | State of growth after 3 weeks | | Evaluation of growth |
|---|---|---|---|---|---|---|
| | | | | Colored green | Germinated | |
| 1 | Sustained-release granule of sucrose with 8% coating, 1% | Hyponex solution | 13,000 lux | 10/10 | 10/10 | 5 |
| 2 | Sustained-release granule of sucrose with 8% coating, 3% | Hyponex solution | 13,000 lux | 10/10 | 10/10 | 5 |
| 3 | Sustained-release granule of sucrose with 8% coating, 6% | Hyponex solution | 13,000 lux | 10/10 | 10/10 | 5 |
| 4 | Sustained-release granule of sucrose with 8% coating, 12% | Hyponex solution | 13,000 lux | 10/10 | 10/10 | 5 |
| 5 | Not contained | Hyponex solution | 13,000 lux | 10/10 | 10/10 | 4 |
| 6 | Sustained-release granule of sucrose with 8% coating, 1% | Hyponex solution | 2,000 lux | 10/10 | 10/10 | 4 |
| 7 | Sustained-release granule of sucrose with 8% coating, 3% | Hyponex solution | 2,000 lux | 10/10 | 10/10 | 5 |
| 8 | Sustained-release granule of sucrose with 8% coating, 6% | Hyponex solution | 2,000 lux | 10/10 | 10/10 | 5 |
| 9 | Sustained-release granule of sucrose with 8% coating, 12% | Hyponex solution | 2,000 lux | 10/10 | 10/10 | 5 |
| 10 | Not contained | Hyponex solution | 2,000 lux | 10/10 | 9/10 | 3 |
| 11 | Sustained-release granule of sucrose with 8% coating, 1% | Hyponex solution | 13,000 lux | 10/10 | 10/10 | 3 |
| 12 | Sustained-release granule of sucrose with 8% coating, 3% | Hyponex solution | 13,000 lux | 10/10 | 10/10 | 3 |
| 13 | Sustained-release granule of sucrose with 8% coating, 6% | Hyponex solution | 13,000 lux | 10/10 | 10/10 | 4 |
| 14 | Sustained-release granule of sucrose with 8% coating, 12% | Hyponex solution | 13,000 lux | 10/10 | 10/10 | 3 |
| 15 | Not contained | Hyponex solution | 13,000 lux | 5/10 | 2/10 | 2 |
| 16 | Sustained-release granule of sucrose with 8% coating and Hyponex, 1% | Distilled water | 13,000 lux | 10/10 | 10/10 | 3 |
| 17 | Sustained-release granule of sucrose with 8% coating and Hyponex, 3% | Distilled water | 13,000 lux | 10/10 | 10/10 | 3 |
| 18 | Sustained-release granule of sucrose with 8% coating and Hyponex, 6% | Distilled water | 13,000 lux | 10/10 | 10/10 | 4 |
| 19 | Sustained-release granule of sucrose with 8% coating and Hyponex, 12% | Distilled water | 13,000 lux | 10/10 | 10/10 | 4 |
| 20 | Not contained | Distilled water | 13,000 lux | 0/10 | 0/10 | 1 |

*1, Withered; 2, Inhibition of growth; 3, poor growth; 4, Slightly poor growth; 5, Normal.

TABLE 4

Germination state of the artificial seed containing a carrot somatic embryo

| Test No. | Content of sustained-release granule | Culture medium | State of growth after 3 weeks | | Evaluation of growth* |
|---|---|---|---|---|---|
| | | | Colored green | Germinated | |
| 1 | Sustained-release granule of sucrose with 8% coating, 1% | Sucrose-free MS liquid culture medium | 9/10 | 5/10 | 4 |
| 2 | Sustained-release granule of sucrose with 8% coating, 3% | Sucrose-free MS liquid culture medium | 10/10 | 10/10 | 5 |
| 3 | Sustained-release granule of sucrose with 8% coating, 6% | Sucrose-free MS liquid culture medium | 10/10 | 9/10 | 5 |

TABLE 4-continued

Germination state of the artificial seed containing a carrot somatic embryo

| Test No. | Content of sustained-release granule | Culture medium | State of growth after 3 weeks | | Evaluation of growth* |
|---|---|---|---|---|---|
| | | | Colored green | Germinated | |
| 4 | Sustained-release granule of sucrose with 8% coating, 12% | Sucrose-free MS liquid culture medium | 10/10 | 8/10 | 4 |
| 5 | Not contained | Sucrose-free MS liquid culture medium | 5/10 | 1/10 | 1 |

*1, Withered; 2, Inhibition of growth; 3, Poor growth; 4, Slightly poor growth; 5, Normal.

What is claimed is:

1. An artificial seed comprising
plant meristematic tissue and
at least one sustained-release granule of sugar comprising a core comprising primarily one or more of a monosaccharide, a disaccharide and a trisaccharide and an outer film comprising 10–90% by weight of an ethylene-vinyl acetate copolymer and 90–10% by weight of a wax, which are encapsulated in a gel matrix.

2. The artificial seed according to claim 1, wherein the copolymerization ratio of the vinyl acetate in the ethylene-vinyl acetate copolymer is in the range of 20–35% by weight.

3. The artificial seed granule of sugar according to claim 1, wherein the number-average molecular weight of the ethylene-vinyl acetate copolymer is in the range of 20,000–40,000.

4. The artificial seed granule of sugar according to claim 1, wherein the ethylene-vinyl acetate copolymer is a terpolymer containing an acid as a third component.

5. The artificial seed granule of sugar according to claim 1, wherein the wax is one having a melting point of 30°–70° C.

* * * * *